United States Patent [19]

Twist et al.

[11] Patent Number: 5,633,230

[45] Date of Patent: May 27, 1997

[54] TREATMENT OF CYTOMEGALOVIRUS INFECTION

[75] Inventors: Michael Twist, deceased, late of Toronto, by Harvey L. Hamburg, Administrator; Martin Sumner-Smith, Bolton, both of Canada

[73] Assignee: Allelix Biopharmaceuticals, Inc., Mississauga, Canada

[21] Appl. No.: 332,518

[22] Filed: Oct. 31, 1994

Related U.S. Application Data

[63] Continuation-in-part of Ser. No. 139,757, Oct. 22, 1993, abandoned, and Ser. No. 995,742, Dec. 22, 1993, abandoned, each is a continuation-in-part of Ser. No.872,398, Apr. 23, 1992, abandoned, said Ser. No. 139,757, is a continuation-in-part of Ser. No. 779,735, Oct. 23, 1991, abandoned, which is a continuation-in-part of Ser. No. 602,953, Oct. 24, 1990, abandoned.

[51] Int. Cl.[6] .................... A61K 38/03; A61K 38/08; A61K 38/10; C07K 7/06

[52] U.S. Cl. ................... 514/15; 514/2; 514/14; 514/16; 514/17; 530/327; 530/328; 530/329; 930/21; 930/290

[58] Field of Search .................. 514/2, 12, 13, 514/14, 15, 16, 17; 530/324, 325, 326, 327, 328, 329; 930/21, 290

[56] References Cited

U.S. PATENT DOCUMENTS

| | | | |
|---|---|---|---|
| 4,447,356 | 5/1984 | Olivera | 530/327 |
| 4,782,966 | 11/1988 | Thackrey | 215/230 |
| 4,837,304 | 6/1989 | Garsky et al. | 530/328 |
| 4,845,195 | 7/1989 | Colonno et al. | 530/330 |
| 4,923,802 | 5/1990 | Gallis | 435/15 |
| 5,093,317 | 3/1992 | Lewis | 514/12 |
| 5,171,838 | 12/1992 | Chiba | 530/326 |

FOREIGN PATENT DOCUMENTS

| | | |
|---|---|---|
| 89/02932 | 4/1989 | WIPO . |
| 89/12461 | 12/1989 | WIPO . |
| 91/09613 | 7/1991 | WIPO . |
| 91/09958 | 7/1991 | WIPO . |
| 92/07871 | 5/1992 | WIPO . |
| 21941 | 11/1993 | WIPO . |

OTHER PUBLICATIONS

Elion "Mechanism of Action and Selectivity of Acyclovir", *The American Journal of Medicine*, pp. 7–13 (1982).

Frankel et al. "Activity of Synthetic Peptides from the TAT Protein of Human Immunodeficiency Virus Type 1", *Proc. Natl. Acad. Sci. USA* 86, pp. 7397–7401 (1989).

Frankel et al. "Cellular Uptake of the TAT Protein from Human Immunodeficiency Virus", *Cell*, 55:1189–1193 (1988).

Geisow et al. "pH in the Endosome: Measurements During Pinocytosis and Receptor–Mediated Endocytosis", *Experimental Cell Research* 150, pp. 36–46 (1984).

Green et al. "Autonomous Functional Domains of Chemically Synthesized Human Immunodeficiency Virus TAT Trans–Activator Protein", *Cell*, 55:1179–1188 (1988).

Green et al. "Mutational Analysis of HIV–1 TAT Minimal Domain Peptides: Identification of Trans–Dominant Mutants that Suppress HIV–LTR–Driven Gene Expression", *Cell*, 58:215–223 (1989).

Hauber et al. "Mutational Analysis of the Conserved Basic Domain of Human Immunodeficiency Virus TAT Protein", *Journal of Virology*, pp. 1181–1187 (1989).

Katsu et al. "Dissipation of Membrane Potential of *Escherichia coli* Cells Induced by Macromolecular Polylysine", *Biochemical and Biophysical Research Communications*, 122:401–406 (1984).

(List continued on next page.)

*Primary Examiner*—Jeffrey E. Russel
*Attorney, Agent, or Firm*—Foley & Lardner

[57] ABSTRACT

Described herein are anti-cytomegalovirus peptides. In a preferred embodiment, the peptide is acetyl-[D-Arg]$_9$-NH$_2$. The use of these peptides, either per se or in combination with other anti-CMV compounds, is disclosed as an effective method for controlling CMV infection.

15 Claims, 4 Drawing Sheets

OTHER PUBLICATIONS

Kuppuswamy et al. "Multiple Functional Domains of TAT, the Trans–Activator of HIV–1, Defined by Mutational Analysis", *Nucleic Acids Research*, 17(9):3551–3559 (1989).

Morad et al. "Binding Sites and Endocytosis of Heparin and Polylysine are Changed When the Two Molecules are Given . . . ", *Biochimica et Biophysica Acta*, 801:117–126 (1984).

Nahata "Antiviral Drugs: Pharmacokinetics, Adverse Effects, and Therapeutic Use", *Journal of Pharmacy Technology*, pp. 100–108 (1987).

Pistocchi et al. "Transport and Subcellular Localization of Polyamines in Carr Protoplasts and Vacuoles", *Plant Physiol*, 87:514–518 (1988).

Ratner et al. "Complete Nucleotide Sequence of the AIDS Virus, HTLV–III", *Nature*, 313:277–284 (1985).

Roy et al. "A Bulge Structure in HIV–1 TAR RNA is Required for TAT Binding and TAT–Mediated Trans–Activation", *Genes and Development*, 4:1365–1373 (1990).

Ruben et al. "Structural and Functional Characterization of Human Immunodeficiency Virus TAT Protein", *Journal of Virology*, pp. 1–8 (1989).

Ryser et al. "Methotrexate–Poly(Lysine) as a Selective Agent for Mutants of Chinese Hamster Ovary Cells Defective in Endocytosis", *Journal of Cellular Physiology*, 135:277–284 (1988).

Wagner et al. "Fibronectin–Coated Beads are Endocytosed by Cells and Align with Microfilament Bundles", *Experimental Cell Research*, 140:373–381 (1982).

Weeks et al. "Fragments of the HIV–1 TAT Protein Specifically Bind TAR RNA", *Science*, 249:1281–1285 (1990).

Docherty "Inactivation of Herpes Simplex Virus . . . ", Antimicrob. Agents Chemotherapy, 31(10):1562–6 (1987).

Webster et al, eds., Encyclopedia of Virology, vol. 1, published 1994 by Academic Press (San Diego), pp. 297–298.

Wyngaarden et al, eds., Cecil Textbook of Medicine, 19th ed., published 1992 by W. B. Saunders Co. (Phil.), p. 1837.

TREATMENT OF CYTOMEGALOVIRUS INFECTION

This is a continuation-in-part of U.S. Ser. No. 08/139,757 filed Oct. 22, 1993, now abandoned, which is a continuation-in-part of U.S. Ser. No. 07/872,398 filed Apr. 23, 1992, now abandoned, and a continuation-in-part of U.S. Ser. No. 07/779,735 filed Oct. 23, 1991, now abandoned, which is a continuation-in-part of U.S. Ser. No. 07/602,953 filed Oct. 24, 1990, now abandoned. This is also a continuation-in-part of U.S. Ser. No. 07/995,742 filed Dec. 22, 1992, now abandoned, which is a continuation-in-part of U.S. Ser. No. 07/872,398, filed Apr. 23, 1992, abandoned.

This invention relates to anti-viral compounds, and particularly to the use of peptide-based anti-viral agents for the treatment of cytomegalovirus infection.

BACKGROUND OF THE INVENTION

Cytomegalovirus (CMV) is a member of the herpes virus family, other well-known members of which include herpes simplex virus, types I and II, Epstein-Barr virus and Varicella Zoster virus. Although these viruses are related taxonomically as double-stranded DNA viruses, each manifests in a clinically distinct manner. In the case of CMV, medical conditions arising from congenital infection include jaundice, respiratory distress and convulsive seizures which may result in mental retardation, neurologic disability or death. Infection in adults is frequently asymptomatic, but may manifest as mononucleosis, hepatitis, pneumonitis or retinitis, particularly in immunocompromised patients such as AIDS sufferers, chemotherapy patients and organ transplant patients undergoing tissue rejection therapy.

A variety of drugs have been developed to treat herpesvirus infection, including natural occurring proteins and synthetic nucleoside analogs. For example, the natural antiviral protein, interferon, has been used in the treatment of herpesvirus infections, as have the nucleoside analogs, cytosine-arabinoside, adenine arabinoside, iodoxyuridine and acyclovir, which is presently the treatment of choice for herpes simplex type I infection.

Unfortunately, drugs such as acyclovir that have proven effective to treat infection by certain herpesviruses are not sufficiently effective to treat CMV. And, drugs currently used to treat CMV infection, such as 9-[(1,3-dihydroxy-2-propoxy)methyl]guanine (ganciclovir, DHPG) and phosphonoformic acid (foscarnet), lack the acceptable side effect and safety profiles of the drugs approved for other treatment of other herpesviruses. Moreover, such drugs are ineffective to treat certain strains of CMV that have acquired drug resistance. Thus, despite recent advances in the development of anti-herpesvirus drugs, there remains a need for therapeutic agents effective to treat CMV infection.

In co-pending patent application WO92/07871 (published 14 May 1992), there are disclosed oligopeptides that are effective to control replication of the human immunodeficiency virus (HIV). In co-pending patent application WO93/21941 (published 11 Nov. 1993), there is disclosed the discovery that these oligopeptides are also effective to prevent replication of certain viruses within the herpesvirus family, particularly the herpes simplex viruses. Further investigation of the anti-viral properties of these oligopeptides has now surprisingly revealed their ability to control replication of cytomegalovirus, including human CMV. It has now also been discovered that these oligopeptides act synergistically with current anti-CMV drugs, particularly ganciclovir, to control replication of CMV.

Accordingly, it is an object of the present invention to provide a method useful to control CMV replication, and further to provide a method for controlling cytomegaloviral infection in a mammal.

It is another object of the present invention to provide pharmaceutical compositions and combinations useful to treat cytomegaloviral infection.

SUMMARY OF THE INVENTION

Accordingly, there is provided in one aspect of the present invention, a method for controlling cytomegalovirus infection in a mammal, which comprises the step of administering to the mammal a composition containing a therapeutically effective amount of a compound of Formula (I):

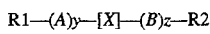

$$R1\text{—}(A)_y\text{—}[X]\text{—}(B)_z\text{—}R2$$

wherein

R1 is H or an N-terminal protecting group;

R2 is OH or a C-terminal protecting group;

X represents an oligopeptide consisting of 'n' amino acids, wherein n is an integer from 6 to 12, said oligopeptide comprising at least one D-amino acid and having a net positive charge selected from n, n−1 and n−2;

y is 0 or 1;

z is 0 or 1; and

A and B collectively represent from 1 to 20 amino acid residues.

In embodiments of the invention, the administered compound is one in which both y and z are 0, and X is an oligopeptide consisting of 7 to 10 basic amino acids in the D-isomer form.

For use in controlling cytomegalovirus infection in a patient, the present invention further provides, as an article of manufacture, a pharmaceutically acceptable package, such as an ampoule or vial, containing an effective amount of an anti-CMV compound of the invention, the package further comprising an information label or sheet instructing use of the contents for the control of CMV infection.

In another of its aspects, the invention provides a method for controlling CMV infection, in which there is administered to a mammal a therapeutically useful combination of a compound of Formula I and an anti-CMV compound such as phosphonoformic acid or ganciclovir. In a preferred embodiment, such combination therapy entails the administration of synergistically effective amounts of ganciclovir and a compound of Formula I.

Embodiments of the present invention are now described in greater detail with reference to the accompanying drawings in which:

BRIEF REFERENCE TO THE DRAWINGS

DESCRIPTION OF THE INVENTION AND PREFERRED EMBODIMENTS

Figure 1:
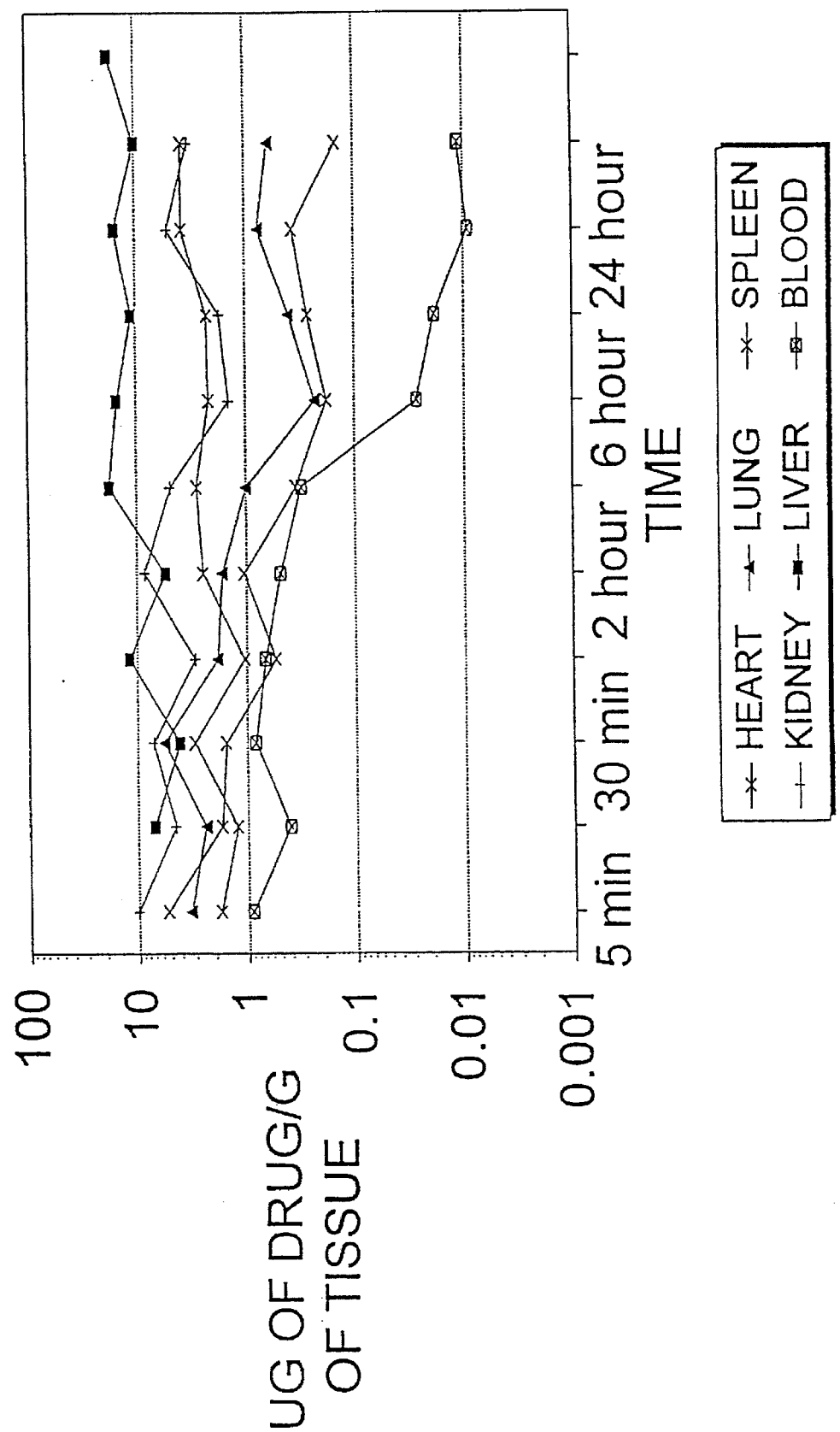
FIG. 1 shows the tissue distribution of a compound according to the present invention when administered by IV injection.

The present invention provides an anti-cytomegaloviral composition that is effective to control CMV infection. Compositions that are effective to "control CMV infection" have the property of slowing, interrupting, arresting or stopping replication of at least one CMV strain, as determined by a cell culture assay used conventionally in the art, such as the well established plaque reduction assay. In the context of the plaque reduction assay for example, the anti-cytomegaloviral nature of a given compound, i.e., its ability to control CMV infection, is indicated by a statistically significant reduction in plaque number and/or size, relative to an untreated control.

The term "cytomegalovirus" is meant to encompass laboratory and other cytomegalovirus strains that infect humans, as well as cytomegalovirus strains that infect other mammals including mice, rats, cats, dogs and horses as well as livestock such as sheep and cattle.

In one aspect of the invention, the anti-CMV compositions of the invention comprise, as active anti-CMV ingredient, a peptidic compound represented by the general Formula (I) provided hereinabove. In a preferred embodiment, the active ingredient is a compound of Formula I in which both y and z are zero, i.e., a compound of Formula (Ia):

$$R1—[X]—R2 \quad\quad (Ia)$$

in which R1, R2 and X are as defined above. Preferred compounds of Formula (Ia) are those in which R1 and R2 are protecting groups, i.e. chemical substituents used commonly in the art of peptide chemistry to stabilize and protect the N- and C-terminal peptide ends from undesired attack, particularly by endogenous exopeptidases. The R1 and R2 groups include chemical substituents attached to the nitrogen atom at the N-terminus of the compound, or the oxygen or carbon atoms of the C-terminal carboxyl group of the compound. By "undesired attack" is meant any type of enzymatic, chemical or biochemical breakdown of the compound at its termini which is likely to affect the function of the compound as an anti-cytomegaloviral agent, i.e. sequential degradation of the compound initiated at a terminal end thereof.

The anti-CMV compounds of the present invention incorporate a core oligopeptide designated 'X' in each of the above formulae I and Ia. Oligopeptide X consists of from 6 to 12 amino acids, coupled for instance by amide linkage. Preferably, X consists of from 7 to 11 amino acids, and in particular, from 8 to 10 amino acids. The amino acid constituents of oligopeptide X are selected to confer on the oligopeptide a net positive charge of 'n', 'n–1' and 'n–2', where 'n' represents the number of amino acids incorporated within oligopeptide X. In other words, X is an oligopeptide consisting either entirely of positively charged amino acids (in the case where the net positive charge is 'n') or of substantially all positively charged amino acids (in the case where the net positive charge is 'n–1' and 'n–2'). The term "net positive charge" refers to the charge on the oligopeptide X as a whole, and is calculated simply by adding the number of positively charged amino acids resident in oligopeptide X and subtracting from that total the number of non-positively charged amino acids resident in oligopeptide X. For instance, an oligopeptide X in which all but one amino acid is positively charged will have a "net" positive charge of 'n–1' in the case where the one amino acid has a neutral charge. The net charge on oligopeptide X will be 'n–2' in the case where the single non-positively charged amino acid is negatively charged rather than neutral. A charge of 'n–2' is also realized when X includes two amino acids carrying a neutral charge and all other amino acids incorporated in X are positively charged. For the purposes of calculating net positive charge, the term "positively charged" refers to an amino acid having a side chain, suitably a β-carbon side chain but desirably an α-carbon side chain, that is cationic in aqueous solution at neutral pH. The term "negatively charged" refers to an amino acid having a side chain that is anionic in aqueous solution at neutral pH. Amino acids having a neutral charge carry a side chain that exhibits either no charge (e.g. alanine) or exhibits both positive and negative charges (e.g. glutamine) in aqueous solution at neutral pH. Preferred compounds for incorporation into the present anti-cytomegaloviral composition are those in which the net positive charge on oligopeptide X is 'n' or 'n–1'.

The terms "amino acid" and "α-amino acid residue" are used interchangeably herein with reference to naturally occurring and synthetic amino acids in either D- or L- form. Unless otherwise stated, the amino acid is the naturally occurring L-amino acid. Included, unless otherwise stated, are: (1) the amino acids having a neutral charge such as glycine; those amino acids having an aliphatic α-carbon side chain such as alanine, valine, norvaline, leucine, norleucine, isoleucine and proline; those having aromatic α-carbon side-chains such as phenylalanine, tyrosine and tryptophan; (2) the negatively charged amino acids, including those having acidic α-carbon side chains such as aspartic acid and glutamic acid; those having side chains which incorporate a hydroxyl group such as serine, homoserine, hydroxynorvaline, hydroxyproline and threonine; those having sulfur-containing α-carbon side chains such as cysteine and methionine; and those having side chains incorporating an amide group such as glutamine and asparagine; and (3) the positively charged amino acids, including those having basic α-carbon side chains such as lysine, arginine, histidine, and ornithine (also herein referred to as "basic amino acids").

According to the present invention, the oligopeptide X comprises at least one amino acid in the D-isomer form. Preferably, oligopeptide X comprises more than one amino acid in D-isomer form to result in a compound comprising, for example, a random combination of L- and D-amino acids, alternating L- and D-amino acids, or alternating blocks of L- and D-amino acids. In a most preferred embodiment, the oligopeptide consists of D-amino acids.

In specific embodiments of the present invention, oligopeptide X in the above Formulae I and Ia has a sequence selected from among the group consisting of;

i) an oligopeptide consisting of from 6 to 11 basic amino acids and one amino acid other than a basic amino acid, wherein each basic amino acid is independently selected from among the group consisting of arginine, lysine, histidine and ornithine, and the single non-basic amino acid is selected from among the group consisting of glutamine, serine, histidine, asparagine and homoglutamine. Especially suitable oligopeptides are those in which each basic amino acid is independently selected from arginine and lysine, and the non-basic amino acid is glutamine; and ii) an oligopeptide consisting essentially of from 7 to 12 basic amino acids, wherein each basic amino acid residue is independently selected from among the group consisting of lysine and arginine.

According to specific embodiments of the present invention, X represents an oligopeptide selected from among the group consisting of:

i) an oligopeptide comprising amino acids arranged in the sequence Arg-Y2-Y3-Arg-Arg-Y4-Arg-Arg-Arg (SEQ ID NO: 1) wherein each of Y2, Y3 and Y4 is a basic amino acid, and at least one of Y2, Y3 and Y4 is arginine;
ii) an oligopeptide comprising 6 to 11 arginines and one glutamine;
iii) an oligopeptide homopolymer consisting of 7 to 12 arginines (SEQ ID NOS: 21–26)

According to preferred embodiments of the present invention, X in the above Formulae I and Ia represents an oligopeptide, preferably consisting essentially of D-amino acids, having an amino acid sequence selected from SEQ ID NOS: 21–26:
Arg-Lys-Lys-Arg-Arg-Lys-Arg-Arg-Arg;
Arg-Lys-Lys-Arg-Arg-Ser-Arg-Arg-Arg;
Arg-Lys-Lys-Arg-Arg-His-Arg-Arg-Arg;
Arg-Lys-Lys-Arg-Arg-Asn-Arg-Arg-Arg;
Arg-Lys-Lys-Arg-Arg-homoGln-Arg-Arg-Arg;
Arg-Lys-Lys-Arg-Arg-Arg-Arg-Arg-Arg;
Arg-Lys-Arg-Arg-Arg-Arg-Arg-Arg-Arg;
Arg-Arg-Lys-Arg-Arg-Arg-Arg-Arg-Arg;
Arg-Arg-Lys-Arg-Arg-Lys-Arg-Arg-Arg;
Arg-Arg-Arg-Arg-Arg-Lys-Arg-Arg-Arg;
Arg-Gln-Arg-Arg-Arg-Arg-Arg-Arg-Arg;
Arg-Arg-Gln-Arg-Arg-Arg-Arg-Arg-Arg;
Arg-Arg-Arg-Gln-Arg-Arg-Arg-Arg-Arg;
Arg-Arg-Arg-Arg-Gln-Arg-Arg-Arg-Arg;
Arg-Arg-Arg-Arg-Arg-Gln-Arg-Arg-Arg;
Arg-Arg-Arg-Arg-Arg-Arg-Gln-Arg-Arg;
Arg-Arg-Arg-Arg-Arg-Arg-Arg-Gln-Arg;
Arg-Arg-Arg-Gln-Arg-Arg;
Arg-Arg-Arg-Arg-Arg-Arg;
Arg-Arg-Arg-Arg-Arg-Arg-Arg;
Arg-Arg-Arg-Arg-Arg-Arg-Arg-Arg;
Arg-Arg-Arg-Arg-Arg-Arg-Arg-Arg-Arg; and
Arg-Arg-Arg-Arg-Arg-Arg-Arg-Arg-Arg-Arg.

Especially preferred are anti-CMV peptides are those in which X in Formulae I and Ia represents an oligopeptide consisting essentially of D-amino acids, and which have a sequence selected from:
D-[Arg-Arg-Arg-Arg-Arg-Arg-Arg-Arg];
D-[Arg-Arg-Arg-Arg-Arg-Arg-Arg-Arg-Arg]; and
D-[Arg-Arg-Arg-Arg-Arg-Arg-Arg-Arg-Arg-Arg].

In another preferred embodiment, compounds of the present invention are those compounds in which R1 and R2 are N- and C-terminal protecting groups conventionally employed in the art of peptide chemistry. Suitable N-terminal protecting groups include, for example, lower alkanoyl groups of the formula R—C(O)— wherein R is a linear or branched $C_{1-5}$ alkyl chain. A preferred group for protecting the N-terminal end of the present compounds is the acetyl group, $CH_3C(O)$—. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$alkyl groups, e.g. methyl, ethyl and propyl groups, while amide-forming groups include amino functions such as primary amines (—$NH_2$), or alkylamino functions, e.g. mono-$C_{1-5}$alkylamino and di-$C_{1-5}$alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine. Of course, N- and C-terminal protecting groups of even greater structural complexity may alternatively be incorporated to protect the N- and C-terminal ends of the compound from attack provided that the anti-cytomegaloviral activity of the compound is not adversely affected by the incorporation thereof, as determined using the plaque reduction assay.

The most preferred anti-CMV peptide is acetyl-[(D-Arg)$_9$]-$NH_2$.

It will be appreciated that the oligopeptide portion of the present compounds may be conjugated, either through its C-terminus or its N-terminus, to other amino acids without necessarily sacrificing the anti-cytomegaloviral activity exhibited by the oligopeptide, as determined by the assays herein described. The present invention thus further embraces anti-cytomegaloviral polypeptide compounds which incorporate the oligopeptides described herein and which conform to the general formula (I), i.e.

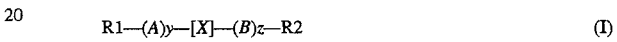

$$R1—(A)y—[X]—(B)z—R2 \qquad (I)$$

wherein at least one of y and z is 1, A and B collectively represent from 1 to 20 amide-linked, amino acids, and preferably from 1 to 10 amino acids, and R1, R2 and X are as specified above.

Specifically contemplated compounds of formula I are anti-cytomegaloviral compounds in which the oligopeptide X is flanked at the C-terminus and/or at the N-terminus by another unit of oligopeptide X, or by partial units of oligopeptide X. The additional units, i.e. A and B, may be linked directly by amide bonding. Alternatively, A and B may comprise peptide linkers of from 1 to about 10 amino acids in length, which bind the additional oligopeptide units to the core oligopeptide X.

Preparation of the anti-CMV peptides is described in the co-pending published patent applications referenced hereinabove, i.e., WO 93/21941 and WO 92/07871 which are incorporated herein by reference, and is not repeated here in great detail. It will nonetheless be readily apparent that, as peptides, the anti-CMV compounds can be prepared by standard, well-established solid-phase peptide synthesis methods (SPPS), general descriptions of which appear, for example, in J. M. Stewart and J. D. Young, *Solid Phase Peptide Synthesis,* 2nd Edition, 1984, Pierce Chemical Company, Rockford, Ill.; and in M. Bodanszky and A. Bodanszky, *The Practice of Peptide Synthesis,* 1984, Springer-Verlag, New York; Applied Biosystems 430A Users Manual, 1987, ABI Inc., Foster City, Calif.

To incorporate N- and/or C-protecting groups, protocols conventional to solid phase peptide synthesis methods can also be applied. To incorporate C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amine as protecting group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine protecting group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxy-benzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g. $C_4$-, $C_8$-, or $C_{18}$-silica. Such column fractionation is generally accomplished by running linear gradients, e.g. 0–50%, of increasing % organic solvent, e.g. acetonitrile, in aqueous buffer, usually containing a small amount of TFA, e.g. 0.1%. Alternatively, ion-exchange HPLC can be employed to separate peptide species on the basis of their charge characteristics. Column fractions are collected, and those containing peptide of the desired/required purity are pooled together. The peptide is typically then treated to exchange the cleavage acid (e.g. TFA) with a pharmaceutically acceptable acid, such as acetic, hydrochloric, phosphoric, maleic, tartaric, succinic and the like, to provide a water soluble salt of the peptide.

For use as an anti-CMV agent, the oligopeptide compounds of the invention are desirably of "pharmaceutical grade" purity, a term used herein with reference to an oligopeptide preparation that migrates as a single peak using HPLC, exhibits uniform and authentic amino acid composition and sequence upon analysis thereof, and otherwise meets standards set by the various national bodies which regulate quality of pharmaceutical products. It will be appreciated that strict standards of purity may not be required for use of the present compounds and compositions in laboratory research and in the veterinary field.

For use in controlling CMV infection, the chosen anti-CMV peptide is formulated in an effective amount with an appropriately selected carrier. The expression "an effective amount" is meant to encompass amounts of the anti-CMV peptide sufficient to prevent or cause a reduction in cytomegaloviral replication. For in vitro use, for instance to control CMV infection in cultured cells, the carrier may simply be culturing medium appropriate for maintaining the cells under culture. In this instance, the effective amount of anti-CMV peptide is that which yields a concentration in the medium sufficient to inhibit CMV replication in the cultured host.

For therapeutic use, the chosen anti-CMV peptide is formulated with a carrier that is pharmaceutically acceptable and is appropriate for delivering the peptide by the chosen route of administration. Such pharmaceutical compositions contain the chosen peptide in a therapeutically effective amount, i.e., an amount sufficient to reduce CMV burden in the patient being treated. Such reduction is most properly revealed by assaying virus titer in samples of biological fluid, such as blood and urine, obtained from the patient before and after treatment.

Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. The compounds herein designated as preferred compounds are substantially water-soluble. Water solubility of these and other compounds of the invention may be enhanced, if desired, by incorporating a solubility enhancer, such as cetyltrimethylammonium bromide or chloride.

For use in controlling CMV infection in a mammal including a human, the present invention provided in one of its aspects a package, in the form of a sterile-filled vial or ampoule, that contains a therapeutically effective amount of the anti-CMV peptide, in either unit dose or multi-dose amounts, wherein the package incorporates a label instructing use of its contents for the control of CMV infection. In one embodiment of the invention, the package contains the peptide and the desired carrier, as an administration-ready formulation. Alternatively, and according to another embodiment of the invention, the package provides the anti-CMV peptide in a form, such as a lyophilized form, suitable for reconstitution in a suitable carrier, such as phosphate-buffered saline.

In a preferred embodiment, the package is a sterile-filled vial or ampoule containing an injectable solution which comprises an effective amount of an anti-CMV peptide of the formula R1-[D-Arg]$_9$-R2 wherein R1 and R2 are as defined by Formula I, dissolved in neutral phosphate buffer (pH 6.5"7.5) to a peptide concentration of 0.1–10 mg/mL or greater, e.g. 1–2 mg/mL.

As an alternative to injectable formulations, the stability particularly of the all D-form peptides permits their formulation for administration by other routes. Compositions for topical application, such as eye drops, creams, lotions, or ointments may be useful, as may aerosol inhalable formulations. Oral dosage forms, such as tablets, capsules and the like, formulated in accordance with standard pharmaceutical practise, may also be employed. Cream, lotion and ointment formulations will be useful particularly for application to virally-induced skin lesions. Appropriate triglyceride bases and gels can be used to prepare creams and ointments, which may include conventional surfactants and antimicrobial agents.

The anti-CMV peptides may be administered in conjunction with other therapeutics, for example, other therapeutic agents useful for the treatment of cytomegaloviral infection including, but not limited to, ganciclovir, foscarnet and HMPA. Such a combination therapy may involve administration of discrete compositions containing a single therapeutic, i.e. a composition containing an anti-CMV peptide of the present invention and a second active anti-CMV compound, or may involve administration of a composition containing both the anti-CMV peptide and the second anti-CMV compound. As noted above, such compositions will be prepared with a pharmaceutically acceptable carrier selected for its suitability in delivering the therapeutic agent to the site of infection.

In a preferred embodiment, such combination therapy entails the administration of synergistically effective amounts of ganciclovir and an anti-CMV peptide of the formula R1-[D-Arg]$_9$-R2, wherein R1 and R2 are as defined by Formula I.

The compositions of the invention are administered particularly to treat patients diagnosed with CMV infection. Candidates for treatment are those patients in an immunocompromised condition, including AIDS patients, patients undergoing cancer chemotherapy and organ and tissue transplant patients undergoing tissue rejection therapy. Clinically effective doses of the anti-CMV peptides are determined using clinical trial protocols established for other anti-CMV drugs, such as ganciclovir. It is expected that the dosing schedule will vary during the course of treatment, moving from an initial loading dose at the high end of the effective range to control current infection followed by maintenance at a lower dose and/or frequency to control recurrence. It is anticipated, on the basis of the results reported herein, that an effective treatment regimen for patients infected with cytomegalovirus will require administration, either daily or every other day, of doses in the range of from 0.01 mg to about 5 mg per kg, e.g., between about 0.1 mg/kg to about 4 mg/kg.

Specific embodiments of the present invention are described in more detail in the following examples which are not to be construed as limiting.

EXAMPLE 1

Synthesis of the acetyl-[D-Arg]$_9$-NH$_2$ oligopeptide

The title compound, designated compound AV-9, was synthesized using p-methylbenzhydrylamine (MBHA) resin as solid support to provide the C-terminal blocking amine on the resultant peptide. Synthesis proceeded using D-arginine residues in which the amino function was blocked with the t-BOC group, and the guanidino function was blocked with the Tos group. Couplings were carried out using excess hydroxybenzotriazole (HOBt)-activated ester of BOC-L-Arg(Tos). Removal of the BOC protecting group after each cycle was effected with TFA. When coupling cycles were completed, the resin-bound peptide was treated with 20% acetic anhydride in acetonitrile, to incorporate an acetyl protecting group at the N-terminus thereof. Liberation of peptide from the resin, and removal of Tos groups, were achieved by treatment with hydrofluoric acid, yielding the C-terminally amidated, title compound. After removal of hydrofluoric acid, the resin/peptide mixture was washed with diethyl ether and extracted with aqueous acetic acid. The crude peptide was lyophilized, then reconstituted and fractionated by RP-HPLC on a C$_{18}$ silica column using a gradient of 2–40% acetonitrile in 0.1% TFA. Fractions were collected and checked by analytical RP-HPLC. Those containing ≧95% of the major product were combined and lyophilized. High resolution mass spectrometry showed the product to be the desired compound, characterized as a white to off-white very hygroscopic powder (op. rot. +52°, water sol. ~1 g/mL).

The resulting peptide was formulated as follows: Flint glass vials (Type I, 5 mL, 13 mm) were first prepared by boiling in HPLC-grade water for 10 minutes and allowed to dry in a 65° C. oven. Stoppers (V32, 13 mm) were washed with isopropanol, then boiled in HPLC-grade water for 10 minutes and then dried in a 65° C. oven. The peptide (99.8 mg) was weighed, transferred to a 100 mL Class A volumetric flask, and taken to volume with phosphate buffered saline (PBS). The PBS (pH7.02) was prepared by combining 400 mL of 8 g/L sodium phosphate monobasic (dihydrate), 600 mL of 9.47 g/L sodium phosphate dibasic (anhydrous), and 4.61 g NaCl in a 1L volumetric flask. This solution was taken to volume with HPLC grade water. The peptide solution was then filtered through a 0.22 μm Millex-GV Millipore filter, and aliquotted into 1 mL fractions into clean glass vials, each containing 1 mg of drug solution. The vials were stoppered, capped, crimped, labelled and stored at 4° C.

EXAMPLE 2

Inhibition of CMV replication

The compound of example 1, acetyl-[(D-Arg)$_9$]-NH$_2$ as the acetate salt (hereinafter referred to as AV-9), was formulated as a 10 mM stock in water for in vitro and cell culture procedures. The stock was then diluted into buffers used for specific assays, or into cell culture media.

The following procedures were then used to determine inhibitory effects of AV-9 on the replication of CMV. First, confluent monolayers of the human diploid cell line, MRC-5 (ATCC# CCL 171) in 24 well cell culture plates were pretreated with specified concentrations (20 μM, 10 μM, 5 μM, 2.5 μM, 1.0 μM, 0.5 μM and 0.0 μM) of AV-9 for 24 hours. This was accomplished by diluting the stock peptide solution in growth medium (10% fetal bovine serum and 10 μg/ml gentamicin in Dulbecco's MEM (DMEM)) used to overlay the monolayers.

After pretreatment with AV-9, the monolayers were overlaid with 0.1 ml log$_{10}$ dilutions of virus (CMV strain AD-169) ranging from $10^{-1}$ to $10^{-6}$. Virus was then allowed to adsorb for 1 hour at 37° C. The virus inoculum was removed and the monolayers were overlayed with DMEM containing 2% FBS, 10 ug/ml gentamicin and a specified concentration of AV-9. Virus was next allowed to replicate for 7 to 10 days until the plaques were judged to be well developed, and then the monolayers were fixed and stained with a solution of 1% crystal violet in 1% formaldehyde, 70% ethanol. Finally, plaques (each representing a single viable virion) were counted and checked microscopically.

In a like manner, plaque reduction assays were also performed against other CMV strains and another CMV host, with comparison against ganciclovir (GCV) and foscarnet (FCV). Results were as follows:

TABLE 1

| CMV Strain | Cell Line | AV-9 | IC$_{50}$ (μM) GCV | FCV |
|---|---|---|---|---|
| AD-169 | MRC-5[1] | 2.6 | 1.9 | 96.0 |
| | MRC-5 | 4.8 | <3.6 | — |
| | MRC-5 | 2.7 | 14.4 | — |
| | HFF[2] | 5.8*,** | 5.8*** | — |
| | HFF | 12.0** | 2.0** | — |
| Davis | MRC-5 | 2.3 | — | — |
| Towne | HFF | 8.7** | 6.5** | — |

*CPE assay, all others are plaque reduction assays.
**Without 24 h drug pre-treatment, all other assays were with 24 h drug pre-treatment
[1] human embryonic lung
[2] human foreskin fibroblast

EXAMPLE 3

Inhibition of Drug-Resistant CMV strains

The anti-CMV activity of peptide AV-9 was evaluated against two ganciclovir-resistant and two foscarnet-resistant laboratory strains of human CMV in the continuous, human embryonic lung cell line MRC-5.

To perform the studies, peptide AV-9 was dissolved as a solid in sterile, deionized water to a final stock concentration of 10 mM. This stock solution was subsequently diluted in cell culture medium to obtain the test concentrations used in the study. Ganciclovir (GCV) was dissolved in sterile, deionized water, and the drug concentration measured spectrophotometrically (7.8mM). Foscarnet (phosphonoformic acid, PFA) was dissolved in sterile, deionized water to a final concentration of 100 mM. Aliquots of the stock solutions were stored at −70° C.

Drug-resistant human CMV strains 759$^r$D100, GDG$^r$K17, PFA$^r$D100 and PFA$^r$B300 were obtained from Dr. Donald M. Coen, Harvard Medical School, Boston, Mass. These strains were generated in the laboratory from the standard CMV strain AD-169 via multiple passages in the presence of either ganciclovir or foscarnet.

Anti-CMV activity of peptide AV-9, ganciclovir (GCV) and foscarnet (PFA) was assessed by standard plaque reduction assay using 24-well microtiter plates. The drug stock solutions were diluted with fresh culture medium to obtain the desired test concentrations in the range 0.5–2500 μM.

MRC-5 cells ($4–5\times10^5$ per well) were grown for 24 hours at 37° C. in 5% $CO_2$ atmosphere in D-MEM/F-12FBS medium containing varying concentrations of drug. At the end of the pre-treatment period, the cells were infected with a suspension containing 50 plaque forming units of CMV (MOI=0.0001). The virus was allowed to absorb for 60 minutes at 37° C. in the absence of drug, at which time the virus innoculum was washed away, and the cells fed with fresh growth medium containing drug. The cells were incubated for 7 to 10 days, until viral plaques were visible. The D-MEM/F-12/FBS medium ±drug was replaced with fresh 1 mL aliquots on a routine basis during the incubation period. Cell cultures were inspected visually for evidence of cytopathic effects and/or cytotoxicity. Vital plaques were counted under a microscope after removing the culture medium from the wells, staining the cells with 1.1% Crystal Violet solution, and washing twice with tap water. Positive control cultures were treated either with GCV or PFA. Negative control cultures were treated as above with D-MEM/F-12/FBS medium only.

Formation of viral plaques was used as an indication of CMV infection. The absence or a reduction in the number of plaques relative to untreated, control cultures indicated an inhibition of virus replication. $IC_{50}$ and $IC_{90}$ values, the concentrations of drug required to inhibit CMV replication by 50% and 90% respectively, were calculated.

In summary, the results showed that peptide AV-9 exhibited appreciable inhibitory activity versus both the ganciclovir-resistant CMV strains 759$^r$D100 and GDG$^r$K17, and the foscarnet-resistant CMV strains PFA$^r$D100 and PF$^r$B300 in a standard plaque reduction assay when host cells were treated with drug, both pre- and post-infection. $IC_{50}$ values for peptide AV-9 ranged from 1.3 to 2.1 μM. By comparison, the $IC_{50}$'s for ganciclovir versus strains 759$^r$D100 and GDG$^r$K17 were determined to be 30.5 and 6.1, respectively, while the $IC_{50}$'s for foscarnet versus strains PF$^r$D100 and PFA$^r$B300 in MRC-5 cells were 233.8 and 384.9 μM, respectively.

EXAMPLE 4

Assessment of peptide distribution, in vivo

Figure 2:
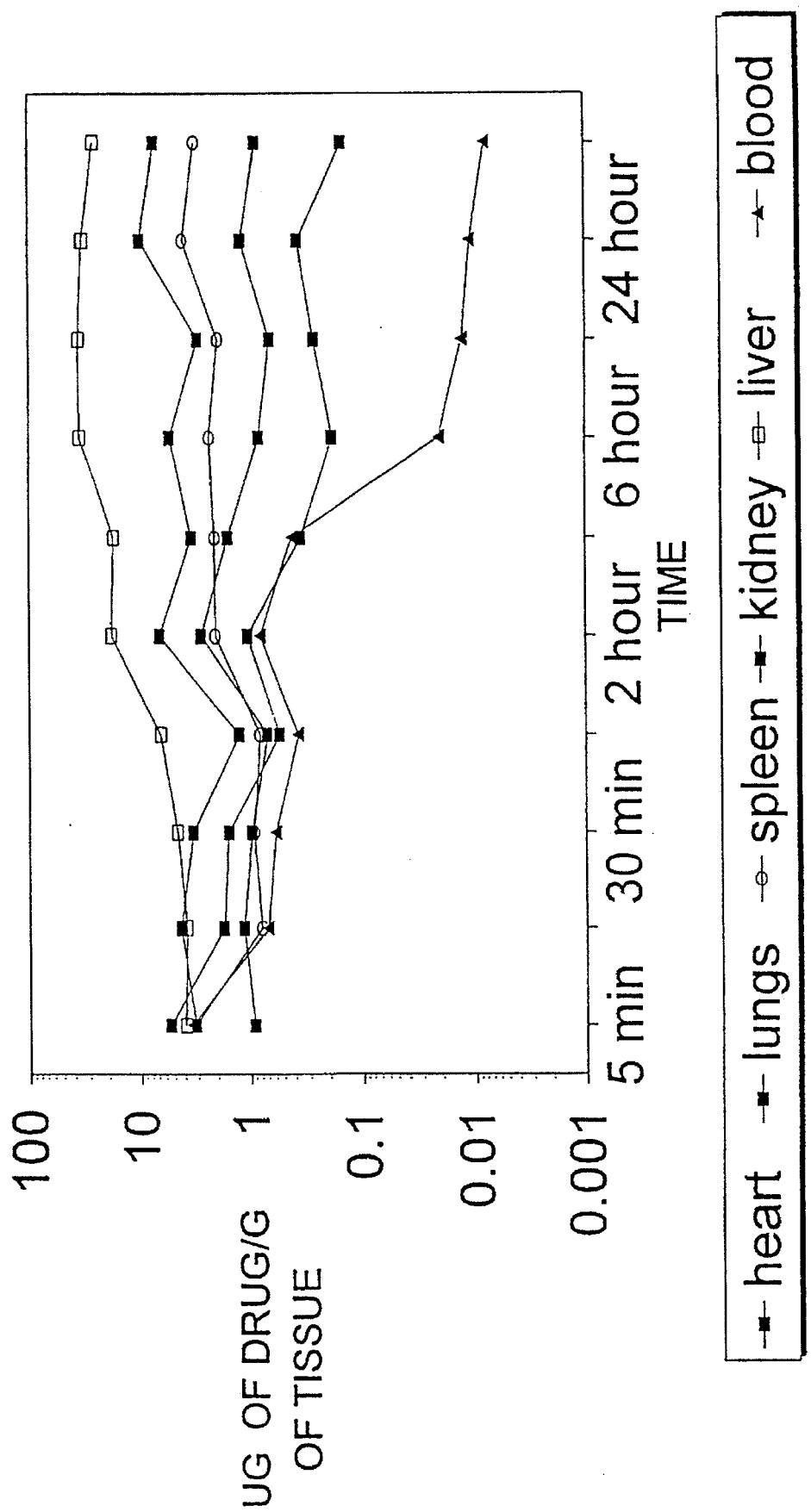
FIG. 2 shows the tissue distribution of the FIG. 1 compound when administered by subcutaneous injection.

The distribution and localization of a $^{14}$C-acetyl form of peptide AV9 was determined following administration by intravenous and sub-cutaneous injection. Ten mice were injected intravenously in the tail vein with 0.25 mL of a solution of 26 μg of $^{14}$C-labelled compound in 10 mL PBS, and ten mice were given the same dose by subcutaneous injection in the abdomen. One mouse from each group was sacrificed at the time points noted in FIGS. 1 and 2, and the noted organs were weighed and digested to homogeneity for scintillation counting. Counts were measured and used to calculate the amount and concentration of drug in each organ. It will be noted that both i.v. and s.c. injection bring about rapid distribution of drug to tissues. The highest and most prolonged levels are attained in the liver, followed by the kidneys and spleen.

Blood levels in mice resulting from single subcutaneous injection of a 53 μg dose of the labelled compound were also evaluated. It was revealed that near-peak blood levels around 1 μg/ml were reached 5 minutes following injection. Peak levels were maintained for about 20 minutes. At 40 minutes and 2 hours, blood levels had declined to about 80% of peak values. A rapid decline in blood levels followed, so that the 4 hour level was about 10% of the peak, and blood levels further declined to the threshold of detection at 8 hours and 24 hours. Evidently, the compound AV-9 reaches the bloodstream rapidly. Near peak levels are maintained for 20–120 min, and the drug is then cleared rapidly from blood.

EXAMPLE 5

Assessment of anti-CMV activity, in vivo

The anti-CMV activity of compound AV-9 was evaluated in mice which had been immunosuppressed by cyclophosphamide. This immunosuppression model mimics the human patient situation, wherein the HCMV-induced disease in immunosuppressed individuals can often be fatal. The particular model used for evaluating potential antiviral activity has been described by Smee et al in J. Infect. Dis., 1991, 164: 958.

The Smith strain of murine CMV, obtained originally from the American Type Culture Collection (Rockville, Md.) was used. A mouse salivary gland preparation was used for the virus pool. An inoculation of $2\times10^4$ plaque forming units of the virus was used in the antiviral study. Female BALB/c mice weighing 10–12 g were quarantined 24 hr prior to use, and maintained on Wayne Lab Blox and tap water ad libitum the duration of the study.

Peptide AV-9 was provided in phosphate buffered saline at a concentration of 1.7 mg/ml. Ganciclovir (DHPG) was purchased from a commercial source, and cyclophosphamide was purchased from Sigma Chemical Co. (St. Louis, Mo.).

To determine tissue virus titre, homogenates of infected mouse organs were titrated for virus using C127/I cells in 96-well microplates. Each tissue sample was homogenized and titrated separately with 3 micro wells used per dilution; plates were read by microscopic examination for viral-induced cytopathic effect, with 50% end points determined by the Reed-Muench method. Mean viral titers were expressed at 50% cell culture infectious doses ($CCID_{50}$)/ gram of tissue.

The mice were immunosuppressed by intraperitoneal (i.p.) injection with 100 mg/kg/day of cyclophosphamide administered on days −1, +3, +6, +10, +14 and +18 relative to virus inoculation. For treatment, peptide AV-9 was administered i.p. in doses of 2.0, 0.7, 0.2 and 0.07 mg/kg/day on days −2, 0, 2, 4, 6, 8 and 10. In a second portion of the study, the compound was administered i.p. in a dose of 0.1 mg/kg/day once daily from day −2 through +10. Ganciclovir in a dose of 50 mg/kg/day was injected i.p. once daily for 10 days beginning 24 hr post-virus exposure (days +1→+10). A total of 15 infected mice/dose were used. Five were designated to be killed on day +9 for determination of virus titers in spleen, lung and salivary gland. The remaining 10 were to be held for 33 days with deaths recorded daily. Five toxicity control mice were used at each dose; these mice were treated in parallel with the infected mice, and were weighed on the initial day of treatment and again 24 after the final treatment. They, too, were observed for a 33-day period. Normal controls were weighed and held in parallel with the toxicity controls. A total of 30 placebo-treated, infected mice were run in parallel as virus controls. Of these, 10 mice were killed for virus titer determinations in their tissues.

Figure 3:
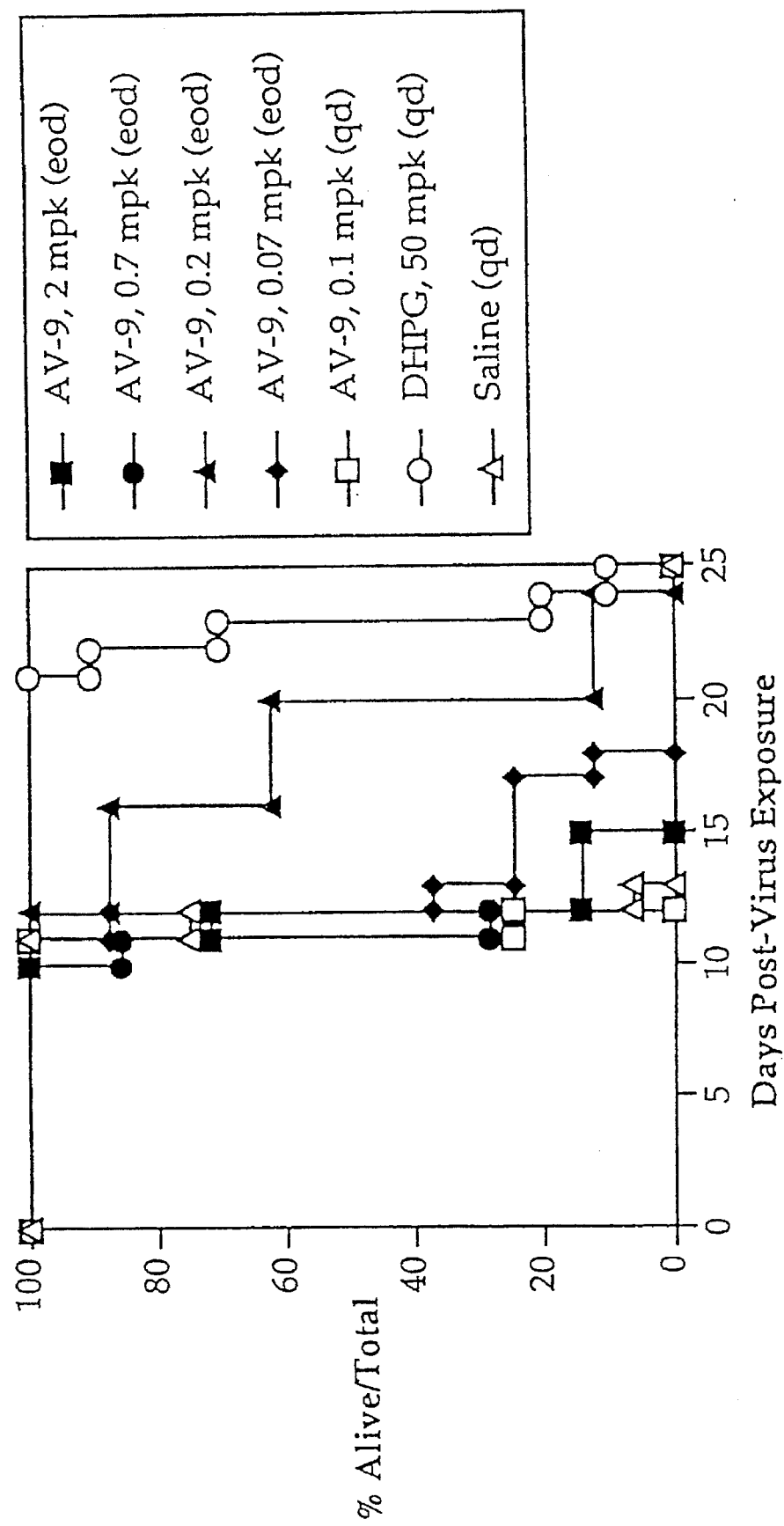
FIG. 3 shows the death pattern of murine CMV-infected, cyclophosphamide-immunosuppressed mice treated with a compound of the invention, and with ganciclovir.

For statistical evaluation, increases in mean day to death and reductions in viral titers were assessed using the two-tailed Mann-Whitney U test. Total survivor increases were evaluated by chi square analysis with Yates'. The results of this study are summarized in Tables 2 and 3 and in FIG. 3.

seen in this study is summarized in FIG. 3. The animals began dying after treatment had terminated; this was seen in both the peptide AV-9 and the DHPG-treated animal and is an anticipated occurrence resulting from virus remaining in the tissues after chemotherapy ceased which, in the immunocompromised animal, will eventually kill the mouse. The peptide AV-9 treatment at this dose also reduced splenic virus titers; of the five animals sampled, three had no detectable virus in their spleens, and one had a titer of $10^{2.5}$, while the last animal had a spleen titer of $10^{5.0}$. Assuming the three spleens having undetectable virus titers at the minimum dilution used ($10^{-2.5}$) had titers of "0", the mean titer was markedly less than that seen in the placebo (P<0.01). Among the lungs of the AV-9 treated group, one had no detectable virus, with the result that the mean titer was reduced by 0.6 $\log_{10}$ in the lungs compared to the placebo-treated controls. No effect was seen on salivary gland virus titers.

Treatment with the lowest dose (0.07 mg/kg/day) of peptide AV-9 administered on an every other day schedule also resulted in a moderately significant increase (P<0.05) in mean survival time (Table 2, FIG. 3).

Although 10 animals were used in each drug-treated group, with 20 assigned as virus controls, it can be noted in Table 2 that less than these numbers are shown in the "Surv/Total" column. On the day animals were to be killed

TABLE 2

| Compound | Dose (mg/kg/day) | Surv/ Total | Mean Day to Death ± S.D. | Tissue Virus Titer ± S.D. ($\log_{10}$ CCID50/g)[b] | | |
|---|---|---|---|---|---|---|
| | | | | Spleen | Lung | Salivary Gland |
| AV-9 | 2.0[c] | 0/7 | 12.1 ± 1.3 | | | |
| | 0.7[c] | 0/7 | 11.6 ± 1.6 | | | |
| | 0.2[c] | 0/8 | 18.5 ± 3.7** | 1.5 ± 2.26** | 3.3 ± 1.9 | 7.6 ± 1.2 |
| | 0.07[c] | 0/8 | 13.4 ± 2.6* | | | |
| | 0.1[d] | 0/8 | 11.3 ± 0.5 | | | |
| DHPG | 50[e] | 0/10 | 22.9 ± 1.1** | 0.5 ± 1.2** | 0 ± 0.0** | 3.5 ± 0.9** |
| Saline | — | 0/16 | 11.8 ± 0.5 | 4.1 ± 0.4 | 3.9 ± 0.5 | 6.4 ± 1.0 |

[a]Cyclophosphamide (100 mg/kg/day) was administered i.p. on days −1, +3, +6, +10, +14, and +18 relative to virus inoculation.
[b]Determined 9 days after virus challenge.
[c]Treatments were given on days −2, 0, +2, +4, +6, +8, and +10 relative to virus inoculation.
[d]Treatments were given on days −2, −1, and 0 through +10.
[e]Treatments were given on days +1 through +10.
*P < 0.05, **P < 0.01 as compared to saline controls.

TABLE 3

| Compounds | Dose (mg/kg/day) | Surv/Total | Mean Body Weight Change[b] (g) |
|---|---|---|---|
| AV-9 | 2.0[c] | 5/5 | 1.9 |
| | 0.7[c] | 5/5 | 2.4 |
| | 0.2[c] | 5/5 | 2.2 |
| | 0.07[c] | 5/5 | 2.7 |
| | 0.1[d] | 5/5 | 3.1 |
| DHPG | 50[e] | 5/5 | 4.2 |
| Saline | — | 5/5 | 4.2 |
| Normal Controls | — | 5/5 | 5.2 |

[a]Cyclophosphamide (100 mg/kg/day) was administered i.p. on days −1, +3, +6, +10, +14, and +18 relative to virus inoculation.
[b]Difference in weight between start of treatment and 24 hr after final treatment.
[c]i.p. treatments were given on days −2, 0, +2, +4, +6, +8, +10.
[d]i.p. treatments were given on days −2, −1, and 0 through +10.
[e]i.p. treatments were given on days +1 through +10.

As seen in Table 2, treatment with peptide AV-9 using a dose of 0.2 mg/kg/day administered every other day resulted in a significant increase in mean day to death. The death pattern for virus titer examinations, a number in each group except those receiving DHPG had already died for reasons unrelated to the experimentation.

The known active drug, DHPG, exerted the positive effect expected, with no animals dying until 21 days after initiation of the infection. Although DHPG treatment reduced virus titers significantly, only in the lung was no virus detected. It would be expected that the DHPG animals would have survived longer than the AV-9-treated mice since less virus was present in the DHPG-treated group. It would take additional days for the titers to increase to the point the animals would die. Also, DHPG was administered for one additional day, and was administered at an optimal dose.

Peptide AV-9 appeared reasonably non-toxic in this study (Table 3), with all mice gaining weight during the treatment period. No other signs of toxicity (hunching, prostration, ruffled fur, tremors) were seen.

These results show that peptide AV-9, when administered i.p. on an every other day treatment schedule for a total of 7 treatments beginning 48 hr pre-virus inoculation was significantly inhibitory to MCMV infections in BALB/c mice immunosuppressed by cyclophosphamide. The antiviral effect was seen as increased mean survival time and decreased spleen and lung virus titer. This effect was seen at a dose of 0.2 mg/kg/day. Treatment with the peptide at a dose of 0.07 mg/kg/day administered every other day appeared to also have a moderate antiviral effect based on a significant increase in mean day to death.

EXAMPLE 6

Drug combination study

For use in this study, HCMV strain AD-169 was obtained from the American Type Culture Collection, Rockville, Md. and ganciclovirresistant clinical isolate of HCMV, strain D16, was obtained from Kenneth D. Thompson, Loyola University Medical Center, Maywood, Ill. Host MRC-5 cells were cultured in a medium of Basal Medium Eagle (BME) (GIBCO), fetal bovine serum (FBS) (Hyclone Laboratories), 0.035% $NaHCO_3$ and without antibiotics.

Test medium for dilution of virus and for preparation and dilution of compounds was Dulbecco's modified Eagle medium (DMEM), 2% FBS, 0.1% $NaHCO_3$, 50 μg gentamicin/ml.

For drug combination experiments, each of AV-9, DHPG, foscarnet, and ALT was prepared in test medium at double the highest concentration used. Each of these compound preparations was then diluted by serial 2-fold dilutions in test medium (except for AZT, which was diluted by serial half-log dilutions). A uniform volume of each concentration of peptide AV-9 was placed in each of 8 sterile tubes (56 total tubes). An equal volume of test medium (without compound) was place in one tube of each of the 8-tube sets (to give the 7 final concentrations of peptide without the combination compound). An equal volume of each concentration of the combination compound (DHPG, foscarnet, or AZT) was placed in one tube of each of the 8-tube sets (to give proper final concentrations of the mixtures of peptide and the combination compound). Empty sterile tubes (7) were used to mix equal volumes of test medium, without drug, with each of the 2× concentrations of the combination compound (to give the 7 final concentrations of combination compound without peptide AV-9).

Growth medium was decanted from established monolayers of MRC-5 cells in 24-well tissue culture plates. Compound dilutions were placed in designated wells of the plates at 0.8 ml/well, with test medium only placed in virus control or cell control wells, and the plates were placed at 37° C. Four wells were used for each different compound dilution. After 24 hr of pre-treatment incubation, the medium was aspirated from each well of the plates. One ml of virus, diluted in test medium was placed in each well except those to be used for cell controls or those to be used for toxicity controls. One ml of sterile test medium was placed in each of these cell or toxicity control wells. The plates were centrifuged at 2200 rpm for 30 minutes at room temperature to allow the virus to adsorb. Medium was aspirated from each well of the plates. The proper individual compound concentrations or combinations were placed in test wells (0.8 ml/well, 4 wells/dilution) or in toxicity control wells. Test medium without compound was added (0.8 ml/well) to each cell control and virus control well. All plates were incubated at 37° C. in a moist atmosphere of 5% $CO_2$, 95% air. When virus plaques had formed in virus control wells, the cells were observed microscopically for morphological changes due to compound cytotoxicity, the medium was aspirated from all wells, and the cells were stained by adding 0.3 ml of 0.2% crystal violet in 10% buffered formalin to each well. After 15 minutes, the stain was removed, cells were rinsed in tap water until the water was clear, and the plates were inverted and dried at room temperature. Plaques were counted by use of a dissecting microscope. The plaque counts were entered in the Mac-Synergy™ program of Prichard and Shipman and 3-D plots were made.

In experiments with DHPG-resistant HCMV, growth medium was decanted from established monolayers of MRC-5 cells in 24-well tissue culture plates. The selected concentrations of compounds were added in duplicate to wells of the plates at 0.8 ml/well. Cell controls (2 wells/ plate) each received 0.8 ml of test medium. Plates were placed in a incubator at 37° C. in a moist atmosphere of 5% $CO_2$, 95% air for 24 hr. All medium was aspirated from each plate and 1.0 ml of virus, diluted in test medium was placed in each well except those to be used for cell controls. One ml of sterile test medium was placed in each of these cell control wells. Virus was allowed to adsorb to the cells during centrifugation at 2200 rpm for 30 minutes at room temperature. Medium was aspirated from each well of the plates. Eight tenths (0.8) ml of the proper compound dilution was placed in each of the test wells. Test medium without compound was added (0.8 ml/well) to each cell control and virus control well. Plates were returned to the 37° C. incubator until plaques could be distinguished in the virus control wells. Cells were observed microscopically for morphological changes due to compound cytotoxicity before the medium was aspirated from all wells and the cells stained by adding 0.3 ml of 0.2% crystal violet in 10% buffered formalin to each well. After 15 minutes, the stain was removed and the plates were inverted and dried at room temperature. Plaques were counted by use of a dissecting microscope. Effective dose, 50% endpoint (ED50) was calculated by regression analysis of the viral plaque data.

Figure 4A:
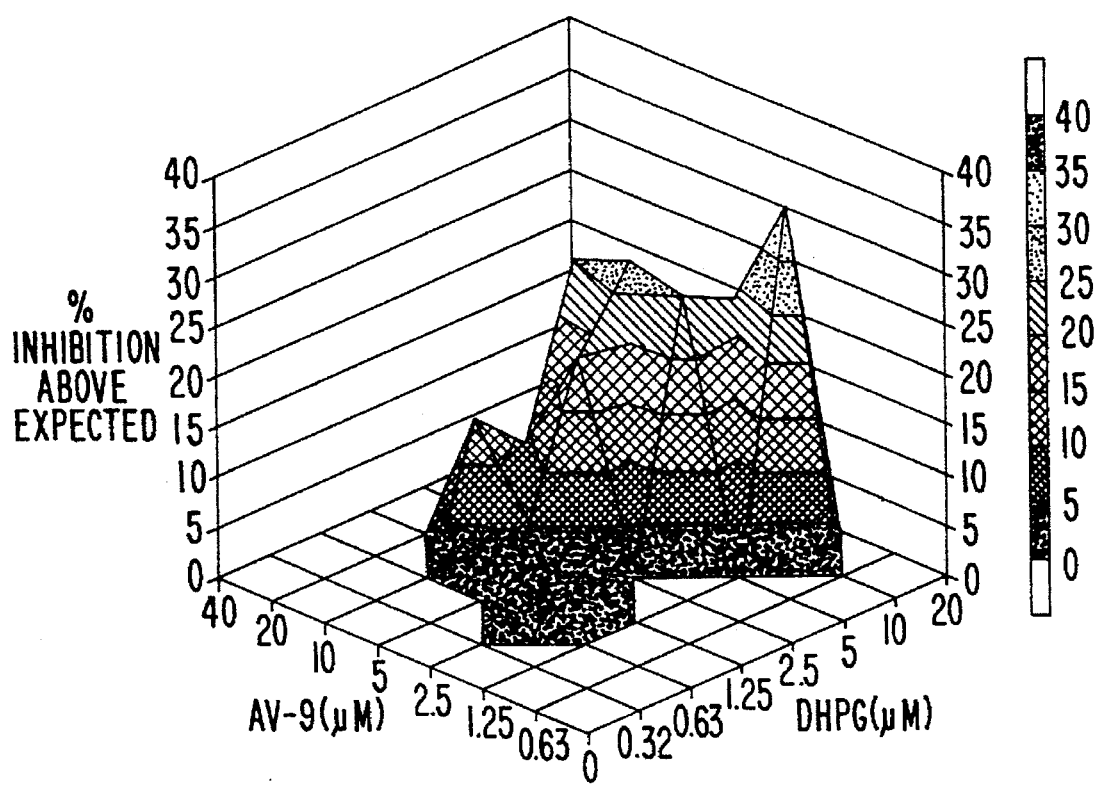
FIG. 4(A) and (B) show the synergy/antagonism plot (A) and contour plot (B) for a combination of compound of the invention and ganciclovir in treatment of human CMV-infected MRC cells.
Figure 4B:
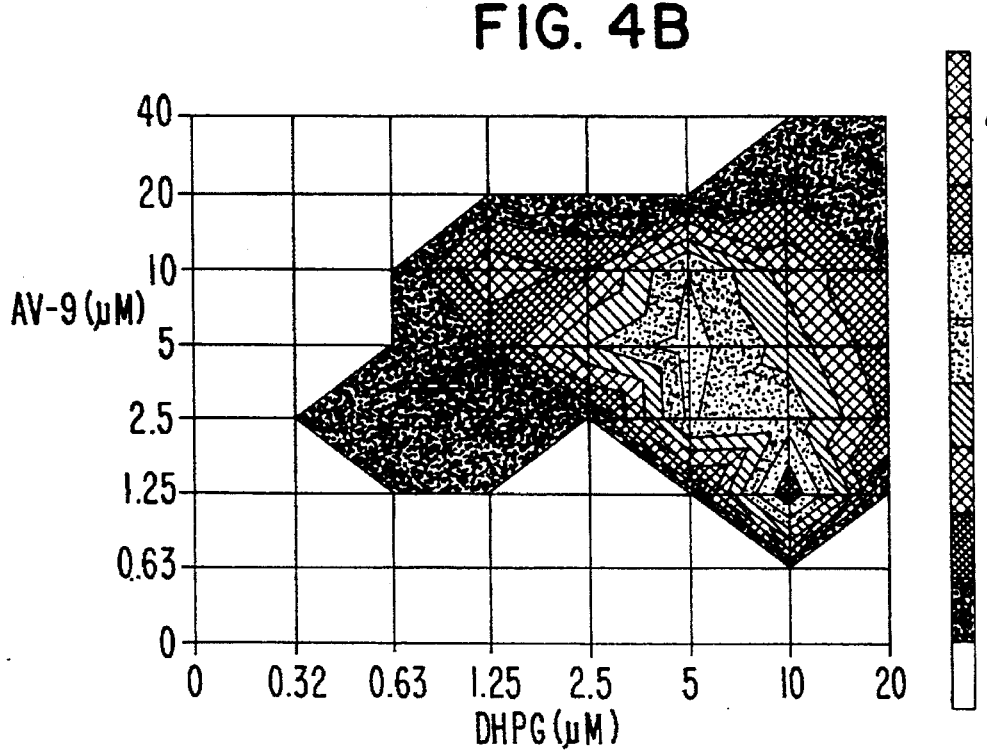

Results of these experiments are shown in FIG. 4. The intense synergy seen when peptide AV-9 was used in combination with DHPG indicates that these compounds work synergistically. When phosphonoformic acid (foscarnet) was used in combination with peptide AV-9, a moderate amount of synergy was seen as well as an insignificant amount of antagonism (not shown). No synergy was seen in the combination of AZT and AV-9.

---

We claim:

1. A method for treating a mammal having a cytomegaloviral infection, comprising the step of administering to said mammal a therapeutically effective amount of a peptide of the formula:

R1—[X]—R2 wherein

R1 is H or an N-terminal protecting group;
    R2 is OH or a C-terminal protecting group; and
    X represents an oligopeptide consisting of 'n' amino acids, wherein
        n is an integer from 6 to 12, said oligopeptide having a net positive charge of 'n', 'n–1' or 'n–2', wherein said oligopeptide comprises at least six arginine residues and no less than n–3 arginine residues and consists essentially of D-amino acids.

2. The method according to claim 1 wherein said oligopeptide is one in which X is an oligopeptide consisting of from 8 to 10 D-arginine residues.

3. The method of claims 1 or 2, further comprising administering to said mammal a therapeutically effective combination of said oligopeptide with an ancillary anti-CMV compound which is ganciclovir or foscarnet.

4. The method according to claim 3, wherein said anti-CMV compound is ganciclovir.

5. The method of claims 1 or 2, wherein said mammal is an immunocompromised condition.

6. The method according to claim 5, wherein said mammal is an AIDS patient.

7. The method according to claim 6, wherein said administration is by injection.

8. A method of claim 5, wherein said immunocompromised condition is AIDS.

9. A method for treating a mammal having a cytomegaloviral infection, comprising the step of administering to said mammal a therapeutically effective amount of a peptide of the formula:

R1—[X]—R2 wherein

R1 is H or an N-terminal protecting group;

R2 is OH or a C-terminal protecting group; and

X represents 9 D-arginine residues.

10. The method according to claim 9, wherein said peptide is acetyl-[D-Arg]$_9$-NH$_2$, or a pharmaceutically acceptable acid addition salt thereof.

11. The method according to claim 9 further comprising administering to said mammal a therapeutically effective combination of said peptide with an anti-CMV ancillary compound which is ganciclovir or foscarnet.

12. The method according to claim 11, wherein said anti-CMV compound is ganciclovir.

13. The method according to claim 11, wherein said mammal is in an immunocompromised condition.

14. The method according to claim 9, wherein said mammal is an AIDS patient.

15. The method according to claim 13, wherein said administration is parenteral.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 9 amino acids
( B ) TYPE: amino acid ( C ) STRANDEDNESS:
        ( D ) TOPOLOGY: linear ( i x ) FEATURE:
        ( A ) NAME/KEY: Modified-site
        ( B ) LOCATION: 2..3
        ( D ) OTHER INFORMATION: /note= "The Xaa at positions 2 and
            3 represents a basic amino acid"

( i x ) FEATURE:
        ( A ) NAME/KEY: Modified-site
        ( B ) LOCATION: 6
        ( D ) OTHER INFORMATION: /note= "The Xaa at position 6
            represents a basic amino acid"

( x i ) SEQUENCE DESCRIPTION: SEQ ID NO:1:

Arg  Xaa  Xaa  Arg  Arg  Xaa  Arg  Arg  Arg
    1                      5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

Arg  Lys  Lys  Arg  Arg  Lys  Arg  Arg  Arg
    1                      5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

Arg  Lys  Lys  Arg  Arg  Ser  Arg  Arg  Arg
    1                      5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

Arg  Lys  Lys  Arg  Arg  His  Arg  Arg  Arg
    1                      5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:5:

Arg  Lys  Lys  Arg  Arg  Asn  Arg  Arg  Arg
    1                      5

( 2 ) INFORMATION FOR SEQ ID NO:6:

( i ) SEQUENCE CHARACTERISTICS:

(A) LENGTH: 9 amino acids
(B) TYPE: amino acid
(C) STRANDEDNESS:
(D) TOPOLOGY: linear (ix) FEATURE:
    (A) NAME/KEY: Modified-site
    (B) LOCATION: 6
    (D) OTHER INFORMATION: /note= "The Xaa at position 6 represents homoGln"

(xi) SEQUENCE DESCRIPTION: SEQ ID NO:6:

Arg Lys Lys Arg Arg Xaa Arg Arg Arg
1                      5

(2) INFORMATION FOR SEQ ID NO:7:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:7:

Arg Lys Lys Arg Arg Arg Arg Arg Arg
1                      5

(2) INFORMATION FOR SEQ ID NO:8:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:8:

Arg Lys Arg Arg Arg Arg Arg Arg Arg
1                      5

(2) INFORMATION FOR SEQ ID NO:9:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:9:

Arg Arg Lys Arg Arg Arg Arg Arg Arg
1                      5

(2) INFORMATION FOR SEQ ID NO:10:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:10:

Arg Arg Lys Arg Arg Lys Arg Arg Arg
1                      5

(2) INFORMATION FOR SEQ ID NO:11:

(i) SEQUENCE CHARACTERISTICS:
    (A) LENGTH: 9 amino acids
    (B) TYPE: amino acid
    (C) STRANDEDNESS:
    (D) TOPOLOGY: linear ( x i ) SEQUENCE DESCRIPTION: SEQ ID NO:11:

Arg Arg Arg Arg Arg Lys Arg Arg Arg
1               5

( 2 ) INFORMATION FOR SEQ ID NO:12:

( i ) SEQUENCE CHARACTERISTICS:
( A ) LENGTH: 9 amino acids
( B ) TYPE: amino acid
( C ) STRANDEDNESS:
( D ) TOPOLOGY: linear ( x i ) SEQUENCE DESCRIPTION: SEQ ID NO:12:

Arg Gln Arg Arg Arg Arg Arg Arg Arg
1               5

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS:
( D ) TOPOLOGY: linear ( x i ) SEQUENCE DESCRIPTION: SEQ ID NO:13:

Arg Arg Gln Arg Arg Arg Arg Arg Arg
1               5

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS:
( D ) TOPOLOGY: linear ( x i ) SEQUENCE DESCRIPTION: SEQ ID NO:14:

Arg Arg Arg Gln Arg Arg Arg Arg Arg
1               5

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS:
( D ) TOPOLOGY: linear ( x i ) SEQUENCE DESCRIPTION: SEQ ID NO:15:

Arg Arg Arg Arg Gln Arg Arg Arg Arg
1               5

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS:
( D ) TOPOLOGY: linear ( x i ) SEQUENCE DESCRIPTION: SEQ ID NO:16:

Arg Arg Arg Arg Arg Gln Arg Arg Arg
1               5

( 2 ) INFORMATION FOR SEQ ID NO:17:

( i ) SEQUENCE CHARACTERISTICS:

(A) LENGTH: 9 amino acids
(B) TYPE: amino acid
(C) STRANDEDNESS:
(D) TOPOLOGY: linear (xi) SEQUENCE DESCRIPTION: SEQ ID NO:17:

Arg Arg Arg Arg Arg Arg Gln Arg Arg
1               5

(2) INFORMATION FOR SEQ ID NO:18:

(i) SEQUENCE CHARACTERISTICS:
(A) LENGTH: 9 amino acids
(B) TYPE: amino acid
(C) STRANDEDNESS:
(D) TOPOLOGY: linear (xi) SEQUENCE DESCRIPTION: SEQ ID NO:18:

Arg Arg Arg Arg Arg Arg Arg Gln Arg
1               5

(2) INFORMATION FOR SEQ ID NO:19:

(i) SEQUENCE CHARACTERISTICS:
(A) LENGTH: 7 amino acids
(B) TYPE: amino acid
(C) STRANDEDNESS:
(D) TOPOLOGY: linear (xi) SEQUENCE DESCRIPTION: SEQ ID NO:19:

Arg Arg Arg Gln Arg Arg Arg
1               5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS:
(D) TOPOLOGY: linear (xi) SEQUENCE DESCRIPTION: SEQ ID NO:20:

Arg Arg Arg Arg Arg Arg
1               5

(2) INFORMATION FOR SEQ ID NO:21:

(i) SEQUENCE CHARACTERISTICS:
(A) LENGTH: 7 amino acids
(B) TYPE: amino acid
(C) STRANDEDNESS:
(D) TOPOLOGY: linear (xi) SEQUENCE DESCRIPTION: SEQ ID NO:21:

Arg Arg Arg Arg Arg Arg Arg
1               5

(2) INFORMATION FOR SEQ ID NO:22:

(i) SEQUENCE CHARACTERISTICS:
(A) LENGTH: 8 amino acids
(B) TYPE: amino acid
(C) STRANDEDNESS:
(D) TOPOLOGY: linear (xi) SEQUENCE DESCRIPTION: SEQ ID NO:22:

Arg Arg Arg Arg Arg Arg Arg Arg
1               5

-continued ( 2 ) INFORMATION FOR SEQ ID NO:23:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:23:

Arg Arg Arg Arg Arg Arg Arg Arg Arg
    1                 5

( 2 ) INFORMATION FOR SEQ ID NO:24:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:24:

Arg Arg Arg Arg Arg Arg Arg Arg Arg Arg
    1                 5                  10

( 2 ) INFORMATION FOR SEQ ID NO:25:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( x i ) SEQUENCE DESCRIPTION: SEQ ID NO:25:

Arg Arg Arg Arg Arg Arg Arg Arg Arg Arg Arg
    1                 5                  10

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( x i ) SEQUENCE DESCRIPTION: SEQ ID NO:26:

Arg Arg Arg Arg Arg Arg Arg Arg Arg Arg Arg Arg
    1                 5                  10